United States Patent [19]

Takemoto et al.

[11] 4,229,446
[45] Oct. 21, 1980

[54] ALUMINUM ACETYLSALICYLATE GLUTAMINATE

[75] Inventors: Yoshinori Takemoto, Yokkaichi; Toshihiro Yasui; Kyoichi Fujii, both of Sakai; Hiroshi Tanaka; Tatsuyuki Hirayama, both of Shizuoka, all of Japan

[73] Assignee: Kyowa Hakko Kogyo Co., Ltd., Japan

[21] Appl. No.: 20,244

[22] Filed: Mar. 13, 1979

[51] Int. Cl.² ............... A01N 37/36; A61K 31/60
[52] U.S. Cl. ............................ 424/230; 260/448 B
[58] Field of Search ................. 260/448 B; 424/230

[56] References Cited

U.S. PATENT DOCUMENTS

| | | | |
|---|---|---|---|
| 2,101,867 | 12/1937 | Miller et al. | 260/448 B X |
| 3,100,787 | 8/1963 | Staib | 424/230 X |
| 3,352,893 | 11/1967 | Holbert | 260/448 B |
| 3,450,752 | 6/1969 | Inklaar | 260/448 R X |
| 3,787,466 | 1/1974 | Kagawa et al. | 260/448 R |
| 3,880,901 | 4/1975 | Turner | 260/448 B |

*Primary Examiner*—Helen M. S. Sneed
*Attorney, Agent, or Firm*—Craig & Antonelli

[57] ABSTRACT

A novel compound, aluminum acetylsalicylate glutaminate having antipyretic, analgesic and anti-inflammatory activities and having little side effects, processes for producing the same and a pharmaceutical composition containing the same are disclosed.

6 Claims, No Drawings

ALUMINUM ACETYLSALICYLATE GLUTAMINATE

DESCRIPTION OF THE INVENTION

This invention relates to a novel compound represented by the general formula:

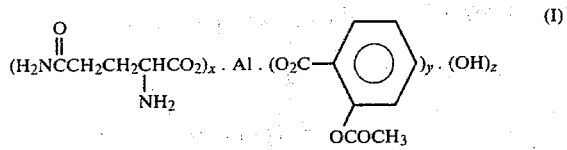

wherein x is 1 or 2, y is 1 or 2, z is 0 or 1 and $x+y+z=3$, and hydrates thereof, a process for producing the compound and an anti-inflammatory agent containing the compound.

Acetylsalicylic acid is a known compound having anti-inflammatory activity and is known as aspirin. Aspirin has been used widely as antipyretic, analgesic and anti-inflammatory agent. However, as is well known, aspirin often induces various side effects such as gastrointestinal disorders.

Various studies have been conducted for reducing the side effects of aspirin, and aluminum acetylsalicylate, mixed agent of aspirin and amino acid and the like have been reported.

On the other hand, glutamine is used as a medicine for treatment of gastric ulcer. Further, aluminum acetylglutaminate which is obtained by reacting N-acetylglutamine with aluminum alkoxide, is also used as a medicine for treatment of gastric ulcer.

Although compounds having anti-inflammatory and analgesic activities are reported besides aspirin, a compound having such activities and less side effects is in demand.

As a result of studies of such compounds, it has been found that the compound represented by the general formula (I) {hereinafter referred to as compound (I)} has such activities and has little side effects. The compound (I) includes the following three compounds:

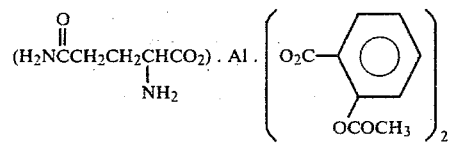

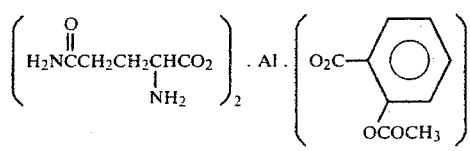

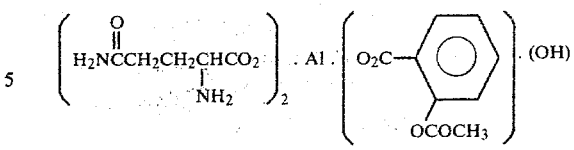

These compounds are produced by the following methods:

(1) The desired compound is produced by reacting acetylsalicylic acid with aluminum alkoxide to form an intermediate reaction product (1) and then reacting the intermediate reaction product (1) with glutamine.

(2) The desired compound is also produced by reacting glutamine with aluminum alkoxide to form an intermediate reaction product (2) and then reacting the intermediate reaction product (2) with acetylsalicylic acid.

Individual compounds A, B and C are obtained by reacting the starting materials in each ratio as follows.

Compound A is obtained by reacting acetylsalicylic acid, glutamine and aluminum alkoxide in either of the above described methods so that these starting materials are in a molar ratio of 2:1:1. Compound B is obtained when the ratio is 1:2:1 and Compound C is obtained when the ratio is 1:1:1. The reactions can be facilitated by using a slightly excess amount of any starting material.

In the Process (1), glutamine is added to the reaction mixture obtained by reacting acetylsalicylic acid with aluminum alkoxide without separating the intermediate reaction product (1) which is considered to be complex of aluminum, and reaction is continued.

In the Process (2), acetylsalicylic acid is added to the reaction mixture obtained by reacting glutamine with aluminum alkoxide without separating the intermediate reaction product (2) which is considered to be complex of aluminum, and reaction is continued.

Examples of aluminum alkoxide utilized in the present invention are aluminum isopropoxide, aluminum methoxide, aluminum ethoxide, aluminum t-butoxide and the like.

The reaction of aluminum alkoxide with acetyl salicylic acid is carried out in a suitable solvent such as methanol, ethanol, isopropanol, benzene, toluene, chloroform, dimethylsulfoxide, and the like.

The reaction of aluminum alkoxide with glutamine is carried out in a suitable solvent such as water, methanol, ethanol, isopropanol, acetone, dimethylsulfoxide, ethyleneglycol and the like. Also, the further reaction of either of the intermediate reaction products (1) or (2) with the remaining starting materials, i.e. acetylsalicylic acid or glutamine may be carried out in the same solvent system, to provide a reaction mixture in which the desired compound (I) is preferably precipitated.

Glutamine is usually utilized by dissolving in water since it is not soluble in organic solvent.

The reactions are carried out at a temperature of 0-90° C. and complete in a short period of time. The desired compound usually precipitates in the reaction mixture.

The desired compound is isolated from the reaction mixture by filtration. When the desired compound does not form a precipitate, it is obtained as a precipitate by the addition of ethanol, isopropanol, etc. to the reaction mixture or is isolated by the concentration of the reaction mixture.

The analgesic, antipyretic, anti-inflammatory activities, etc. of aluminum acetylsalicylate glutaminate will be apparent from the following Experiments.

EXPERIMENT A

Analgesic activities of aspirin and compounds A, B and C

Ten male dd-strain mice weighing 20±1 g for one group are treated with the compounds according to the method of Koster et al. [Koster, R. et al: Fed. Proc., Vol. 18, 412 (1959)]. The test compounds are administered orally to the mice. After 60 minutes of the administration, animals are injected with 0.2 ml of 0.7% acetic acid aqueous solution intraperitoneally. Starting ten minutes after the administration of acetic acid, the number of writhing reaction occurred in ten minutes is counted.

As a control, one group is treated with the same procedures as described above except that test compounds are not administered. The suppression ratios of test groups are shown in Table 1.

The dosages of test compounds are 200 mg/Kg for aspirin, 300 mg/Kg for compound A, 600 mg/Kg for compound B and 400 mg/Kg for compound C. These dosages correspond to 200 mg/Kg of acetylsalicylic acid.

TABLE 1

| Treatment | Suppression ratio |
|---|---|
| Aspirin 200 mg/Kg | 30.3% |
| Compound A 300 mg/Kg | 32.5% |
| Compound B 600 mg/Kg | 29.6% |
| Compound C 400 mg/Kg | 31.0% |

EXPERIMENT B

Antipyretic activities of aspirin and compounds A, B and C

In this experiment, ten male Wistar-strain rats weighing 90–100 g for one group are treated with 2.5 ml/rat of a suspension of yeast (Brewers Yeast, product of Nutritional Biochem. Co. U.S.A.) in physiological saline (concentration: 250 mg/ml), by subcutaneous injection in the back, according to the method of Gleen et al [Gleen, E. M. et. al: J. Pharma. Exp. Therp. 155 157 (1967)]. The animals are then fasted.

The animals showing an increased rectal temperature of 38° C. or more after 17 hours are selected for use in experiment. A solution or suspension of test compound is administered orally in a specified amount. As a control, one group is treated with distilled water alone.

After administration, the rectal temperature is measured at the time indicated. The results are shown in Table 2 below.

TABLE 2

| Treatment | Rectal temperature (°C.) Time after administration (hour) | | | | |
|---|---|---|---|---|---|
| | 0 | 1 | 2 | 4 | 6 |
| Control | 38.4±0.1 | 38.4±0.1 | 38.0±0.1 | 37.8±0.1 | 38.0±0.1 |
| Aspirin 200 mg/Kg | 38.2±0.1 | 37.2±0.1 | 37.0±0.1 | 37.4±0.2 | 37.5±0.1 |
| Compound A 300 mg/Kg | 38.4±0.1 | 37.1±0.1 | 36.8±0.1 | 37.5±0.1 | 37.7±0.0 |
| Compound B 600 mg/Kg | 38.4±0.1 | 37.2±0.1 | 37.0±0.1 | 37.3±0.1 | 35.5±0.1 |

TABLE 2-continued

| Treatment | Rectal temperature (°C.) Time after administration (hour) | | | | |
|---|---|---|---|---|---|
| | 0 | 1 | 2 | 4 | 6 |
| Compound C 400 mg/Kg | 38.2±0.1 | 37.1±0.1 | 37.0±0.1 | 37.4±0.2 | 37.6±0.1 |

EXPERIMENT C

Anti-inflammatory activities of aspirin and compounds A, B and C

In this experiment, six male Wistar-strain rats weighing 140±10 g for one group are treated with test compounds according to the method of Yamaski et al [Folia Farm. Jap., vol. 63, 302 (1967)].

After one hour of oral administration of test compounds, the animals are treated with a phlogistic agent of 0.1 ml of 1% carrageenin solution by subcutaneous injection in a hind paw. Swelling of the paw is measured at the time indicated. As a control, one group is treated with the same procedures as described above except that test compounds are not administered. The suppression ratios of test groups are shown in Table 3 below:

TABLE 3

| Treatment | Suppression ratio (%) Time after administration | |
|---|---|---|
| | 3 hours | 5 hours |
| Aspirin 200 mg/Kg | 43 | 34 |
| Compound A 300 mg/Kg | 52 | 39 |
| Compound B 600 mg/Kg | 52 | 42 |
| Compound C 400 mg/Kg | 50 | 37 |

EXPERIMENT D

Ulcer formation by aspirin and compounds A, B and C

In this experiment, ten male Wistar-strain rats weighting 190±10 g for one group fasted for 24 hours are used. After the pylorus is ligated according to the standard method of Shay et al., the test compounds are orally administered. After 6 hours of the administration, the animals are killed and the stomach are opened. The length of lesions is measured and the results are shown in Table 4 below. The ulcer index expressed by mm indicates the sum of the length of the lesions of each group.

The same procedures as described above are repeated except that male Donryu rats are used instead of male Wistar-strain and the results are shown in Table 4 below.

TABLE 4

| Test compound | Ulcer index | |
|---|---|---|
| | Wistar strain | Donryu strain |
| Aspirin 200 mg/Kg | 32.8 ± 5.0 | 49.3 ± 8.1 |
| Compound A 300 mg/Kg | 0.1 ± 0.4 | 14.9 ± 3.3 |
| Compound B 600 mg/Kg | 11.7 ± 2.0 | 7.2 ± 1.4 |
| Compound C 400 mg/Kg | 6.7 ± 1.5 | 10.2 ± 2.5 |

EXPERIMENT E

LD50 of compounds A and B

In this experiment, ten male dd-strain mice weighing 20±1 g are used. The compounds are administered orally.

The numbers of the animals which died during 7 days after administration are shown in Table 5.

TABLE 5

| The compound | Dose g/Kg | | |
|---|---|---|---|
| | 1 | 3 | 10 |
| Compound A | 0 | 8 | — |
| Compound B | — | 0 | 9 |

$LD_{50}$ of compounds A and B are considered to be as follows.

A: $1 \text{ g/Kg} < LD_{50} < 3 \text{ g/Kg}$
B: $3 \text{ g/Kg} < LD_{50} < 10 \text{ g/Kg}$
$LD_{50}$ of acetylsalicylic acid is 1.6 g/Kg.

As apparent from the results of the above experiments, when compound A, B or C is administered so that the content of acetylsalicylic acid may be the same, antipyretic, analgesic and anti-inflammatory activities of the present compounds are as strong as those of aspirin and the development of gastric lesions by the present compounds is less than that of aspirin.

The present compounds according to the invention may be formulated for administration in any convenient way for use in human and the invention therefore includes within its scope a pharmaceutical composition comprising a compound (I) above together with a pharmaceutical carrier or excipient.

The compositions may be formulated for administration by any route, such as oral, etc. The compositions may be in the form of tablets, capsules, powders, granules, lozenges, creams or liquid preparations such as oral solution or suspension.

Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maizestarch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate.

The tablets may be coated according to methods well known in normal pharmaceutical practice. Oral liquid preparations may be in the form of, for example, syrups or elixirs, or may be presented as a dry product for reconstitution with water or other suitable vehicle before use.

Such liquid preparations may contain conventional additives such as suspending agents, for example sorbitol, methyl cellulose, glucose syrup, gelatin, hydroxyethylcellulose, carboxymethyl cellulose, aluminum stearate gel or hydrogenated edible fats, emulsifying agents, for example lecithin, sorbitan monooleate, or acacia; non-aqueous vehicles for example almond oil, fractionated coconut oil, oily esters such as esters of glycerine, propylene glycol, or ethyl alcohol; preservatives, for example methyl or propyl p-hydroxybenzoate or sorbic acid, and if desired convention flavouring or colouring agents.

The compositions may contain from 1% by weight, preferably from 10-60% by weight, of the active ingredient, depending on the method of administration. Where the compositions comprise dosage units, each unit will preferably contain from 0.1-1 g. of the active ingredient. The dosage as employed for adult human treatment will preferably range from 0.5-2 g. per day as acetylsalicylic acid, depending on the route and frequency of administration.

The present compounds may be the sole therapeutic agent in the compositions of the invention.

Certain specific embodiments of the present invention are illustrated by the following representative examples.

EXAMPLE 1

In this example, 9.0 g of acetylsalicylic acid and 10.2 g of aluminum isopropoxide are dissolved in 150 ml of methanol and the reaction is carried out at a temperature of 5° C. with stirring. After the completion of the reaction, the reaction mixture is subjected to filtration to remove a slight amount of insoluble matter. Then, to the filtrate is added a solution which is obtained by dissolving 14.6 g of glutamine in 200 ml of water. In a short time after starting the addition of the solution, a white precipitates is formed. After the addition, stirring is continued for 30 minutes and then, the resultant mixture is filtered to obtain a precipitate. The precipitate is dried to obtain 22.4 g of a white powder of which the physicochemical properties are shown below.

Elementary analytical values (as $C_{19}H_{25}N_4O_{10}Al.2H_2O$). Calculated: $C=42.9\%$, $H=5.5\%$, $N=10.5\%$, $Al=5.1\%$ Amide state nitrogen$=5.3\%$. Found: $C=42.8\%$, $H=5.5\%$, $N=10.4\%$, $Al=5.2\%$ Amide state nitrogen$=5.2\%$.

Content of water 6.8%

Infrared absorption spectrum, measured in KBr Tablet, shows characteristic absorption at the following wave numbers (cm$^{-1}$) 3410, 1685, 1630, 1588, 1487, 1450, 1414, 1330 and 1200.

From the foregoing, the obtained white powder is identified as aluminum acetylsalicylate bisglutaminate dihydrate and the yield is 84.1%.

EXAMPLE 2

In this example, 18.0 g of acetylsalicylic acid and 10.2 g of aluminum isopropoxide are dissolved in 50 ml of methanol and the reaction is carried out at a temperature of 5° C. with stirring. After the completion of the reaction, to the reaction mixture is added a solution which is obtained by dissolving 7.3 g of glutamine in 100 ml of water. After few minutes from the starting of addition, white precipitates are formed. The mixture is stirred for 30 minutes under ice cooling for the completion of the reaction and crystallization The reaction mixture is subjected to filtration and the residue is washed and dried to obtain 21.0 g of a white powder.

The physicochemical properties of the powder are as follows:

Elementary analytical values (as $C_{23}H_{23}O_{11}N_2.Al.2H_2O$). Calculated: $C=48.8\%$, $H=4.8\%$, $N=5.0\%$, $Al=4.8\%$. Amide state nitrogen$=2.5\%$. Found: $C=48.9\%$, $H=4.7\%$, $N=4.9\%$, $Al=4.7\%$. Amide state nitrogen$=2.4\%$.

Content of Water: 6.4%

Infrared absorption spectrum, measured in KBr Tablet, shows characteristic absorption at the following wave numbers (cm$^{-1}$) 3410, 1755, 1690, 1632, 1610, 1570, 1490, 1457, 1427, 1200

From the foregoing, the obtained white powder is identified as aluminum bis-acetylsalicylate glutaminate dihydrate and the yield is 74.2%.

EXAMPLE 3

In this example, 9 g of acetylsalicylic acid is dissolved in 100 ml of ethanol. To the solution is added 10.2 g of aluminum isopropoxide and the reaction is carried out at a temperature of 5° C. with stirring. After the completion of the reaction, to the reaction mixture is added a hot solution which is obtained by dissolving 7.3 g of glutamine in 80 ml of hot water. The reaction is carried out at a temperature of 5° C. with stirring for an hour.

The reaction mixture is subjected to filtration and the residue is dried to obtain 16 g of a white powder. The physicochemical properties of the powder are as follows:

Elementary analytical values: (as $C_{14}H_{17}O_8N_2Al.2-H_2O$). Calculated: C=41.6%, H=5.2%, N=6.9%, Al=6.7%. Amide state nitrogen=3.5%. Found: C=41.0%, H=5.3%, N=7.0%, Al=6.8% Amide state nitrogen=3.5%.

Infrared absorption spectrum, measured in KBr Tablet, shows characteristic absorption at the following wave numbers. 3410, 1753, 1690, 1630, 1610, 1580, 1490, 1450, 1418, 1333, 1200.

From the foregoing, the powder is identified as mono-hydroxy aluminum acetylsalicylate glutaminate dihydrate and the yield is 79.1%.

EXAMPLE 4

In this example, 14.6 g of glutamine is dissolved in 190 ml of hot water having a temperature of 85° C. To the solution is added 10.2 g of aluminum isopropoxide while stirring. Then, the reaction mixture is cooled quickly. To the mixture is added a solution which is obtained by dissolving 9 g of acetylsalicylic acid in 50 ml of ethanol.

After the completion of reaction, the formed precipitates are filtered and are dried to obtain 19 g of aluminum acetylsalicylate bis-glutaminate as a white powder.

What is claimed is:

1. An aluminum acetylsalicylate glutaminate represented by the general formula:

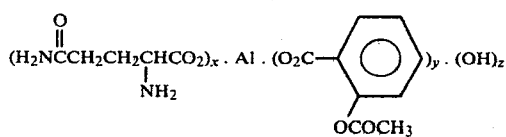

wherein x is 1 or 2, y is 1 or 2, z is 0 or 1 and $x+y+z=3$, and hydrates thereof.

2. An aluminum acetylsalicylate glutaminate according to claim 1, namely aluminum bisacetylsalicylate glutaminate.

3. An aluminum acetylsalicylate glutaminate according to claim 1, namely aluminum acetylsalicylate bis glutaminate.

4. An aluminum acetylsalicylate glutaminate according to claim 1, namely monohydroxy aluminum acetylsalicylate glutaminate.

5. An antipyritic, analgesic and anti-inflamatory composition which comprises an effective amount of an aluminum acetylsalicylate glutaminate represented by the general formula:

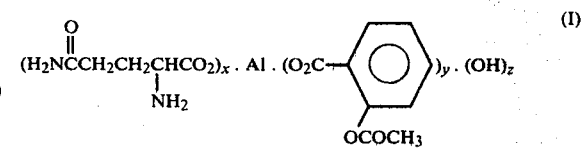

wherein x is 1 or 2, y is 1 or 2, z is 0 or 1 and $x+y+z=3$, and hydrates thereof and a pharmaceutically acceptable non-toxic carrier or excipient.

6. The composition of claim 5, wherein the effective amount of said aluminum acetylsalicylate glutaminate is from 10–60% by weight of the composition.

* * * * *